US011723533B2

(12) United States Patent
Steinmueller (10) Patent No.: US 11,723,533 B2
(45) Date of Patent: Aug. 15, 2023

(54) METHOD AND VISION TESTING SYSTEM FOR TESTING THE EYES

(71) Applicant: OCULUS OPTIKGERAETE GMBH, Wetzlar (DE)

(72) Inventor: Andreas Steinmueller, Wettenberg (DE)

(73) Assignee: Oculus Optikgeraete GmbH, Wetzlar (DE)

( * ) Notice: Subject to any disclaimer, the term of this patent is extended or adjusted under 35 U.S.C. 154(b) by 666 days.

(21) Appl. No.: 16/809,818

(22) Filed: Mar. 5, 2020

(65) Prior Publication Data

US 2020/0281461 A1    Sep. 10, 2020

(30) Foreign Application Priority Data

Mar. 7, 2019    (DE) ...................... 10 2019 105 756.6

(51) Int. Cl.
| | | |
|---|---|---|
| *A61B 3/10* | (2006.01) | |
| *A61B 3/13* | (2006.01) | |
| *A61B 3/107* | (2006.01) | |
| *A61B 3/103* | (2006.01) | |

(52) U.S. Cl.
CPC .............. *A61B 3/102* (2013.01); *A61B 3/103* (2013.01); *A61B 3/1005* (2013.01); *A61B 3/107* (2013.01); *A61B 3/13* (2013.01)

(58) Field of Classification Search
CPC ......... A61B 3/02; A61B 3/1005; A61B 3/103; A61B 3/107; A61B 3/13
USPC ......................................................... 351/221
See application file for complete search history.

(56) References Cited

U.S. PATENT DOCUMENTS

| | | |
|---|---|---|
| 2005/0105047 A1 | 5/2005 | Smitth, III et al. |
| 2017/0189233 A1 | 7/2017 | Dewey et al. |

FOREIGN PATENT DOCUMENTS

| | | |
|---|---|---|
| DE | 4210384 A1 | 10/1993 |
| DE | 102006017389 A1 | 10/2007 |
| DE | 102017210577 A1 | 12/2018 |
| EP | 3210526 A1 | 8/2017 |
| EP | 3222204 A1 | 9/2017 |
| WO | 2015044364 A1 | 4/2015 |

OTHER PUBLICATIONS

European Patent Office, Extended European Search Report, Application No. 20158196.4, dated Jul. 10, 2020, 7 pages.

*Primary Examiner* — Collin X Beatty
*Assistant Examiner* — Grant A Gagnon
(74) *Attorney, Agent, or Firm* — Quarles & Brady LLP (57) ABSTRACT

A method for testing the eyes of a test person with the aid of a vision testing system as well as to a vision testing system, comprising a first measuring device, a second topographic measuring device, a third refractive measuring device and a processing means, a central axial length ($L_Z$) and a peripheral axial length ($L_P$) of an eye of the test person being measured with the aid of said first measuring device, a curvature of the cornea of the eye being measured with the aid of said second measuring device, a refractive property of the eye being measured with the aid of said third measuring device, measurement data of the measurements of the first, second and third measuring device being processed with the aid of said processing means, said processing means outputting the measurement data.

28 Claims, 2 Drawing Sheets

METHOD AND VISION TESTING SYSTEM FOR TESTING THE EYES

CROSS-REFERENCE TO RELATED APPLICATIONS

This application claims priority to German Patent Application No. 10 2019 105 756.6 filed Mar. 7, 2019. The contents of this application are hereby incorporated by reference as if set forth in its entirety herein.

The disclosure relates to a method for testing the eyes of a test person having the features of claim 1 and a vision testing system having the features of claim 17.

Refractive measuring devices are sufficiently known and routinely serve for determining a refraction value of an eye of a test person. The refraction value can be utilised for evaluating an optical ametropia of the eye. A frequent form of ametropia is myopia where a focal plane is in front of the retina, which results in a blurred visual impression. A distinction is made between different forms of myopia. In cases of the so-called axial myopia, an axial length of the eye is increased. In cases of refraction myopia, the refractive power of the refractive parts of the eye, for example the cornea or the lens, is increased. The increased refractive power can, for example, be caused by an increased curvature of a refractive surface, such as the cornea. A refractive index of the lens can also be changed so that an increased refractive power ensues. Myopia can already be developed in childhood due to different environmental factors, such as visual tasks in the close range of the eye, or it can occur with advancing age, for example due to a decrease in the accommodation capability of the ciliary muscle with the lens. Apart from a medication intake, diseases, such as diabetes mellitus, or a genetic disposition may also be a cause of myopia.

With the aid of a refractive measuring device, a refraction value can be objectively determined in diopters (dpt) comparatively easily. For instance, a vision testing system is known from DE 102 006 017 389 A1 that is constructed from a refractive measuring device and from a topographic measuring device. The refractive measuring device in this case is an autorefractometer that is combined with the topographic measuring device that is realised in the manner of a keratometer. With the aid of the keratometer, a topography of the cornea can be determined, which makes it possible to gain information on a possible cause of myopia, for example a supposed cataract.

Nevertheless, evaluating the refraction and topography data that have been obtained in this way is difficult since the refraction measurement may be inaccurate and other influencing factors may also be the cause of certain refraction values. An inaccurate refraction measurement may, for example, arise when the test person's eye accommodates at close range during the measurement. In order to rule this out, the ciliary muscle can be paralysed by medication (cycloplegia), which, however, is time-consuming and unpleasant for the test person.

In cases of axial myopia, the central axial length of the eye is increased, which also leads to the wall structures of the eye, in particular the retina, being stretched. This stretching then also affects the peripheral (equatorial) retina. In the region of the peripheral retina, the peripheral refraction value may therefore differ from a central refraction value that is measured centrally on the visual axis. If an axial myopia is corrected with the aid of a pair of glasses or contact lenses, a focal plane or a focus is shifted onto the retina, in particular in the macula region, on the visual axis. Since, however, a refraction value frequently differs in the peripheral region of the retina in cases of axial myopia, the focal plane or a focus is shifted behind the retina in the peripheral region via the correction with the aid of the pair of glasses or contact lenses. Since the focal plane matches the shape of the retina in the case of a healthy eye, the focal plane has the shape of a cup or corresponds to a focal cup. In the case of the correction with the aid of the pair of glasses or contact lenses, this focal cup is then only on the retina in the region of the macula and is shifted behind the retina in the peripheral region of the retina so that the myopia has then been overcorrected in the peripheral region.

During the growth of the eyes in childhood, such a correction of an axial myopia can, however, lead to the growth of the eye ball being influenced in such a manner that a length of the eye ball continues to increase and that the axial myopia consequently advances more quickly. Since the eye grows towards the focus of the lens in this growth stage, the general assumption is that a visual aid prevents a correction of the eye through growing. A shift of the focal cup in the peripheral region behind the retina apparently promotes this undesirable growth development of the eye. It can be assumed that a progression of an axial myopia can be slowed down if the focal cup can be shifted in front of the retina in the peripheral region of the retina with the aid of a visual aid.

The present disclosure is therefore based on the object of proposing a method and a vision testing system with the aid of which refractive properties of an eye can be determined more precisely.

This object is attained by a method having the features of claim 1 as well as by a vision testing system having the features of claim 17.

The disclosed method for testing the eyes of a test person is carried out with the aid of a vision testing system that comprises a first interferometric measuring device, a second topographic measuring device, a third refractive measuring device and a processing means, a central axial length and a peripheral axial length of an eye of the test person being measured with the aid of said first measuring device, a curvature of the cornea of the eye being measured with the aid of said second measuring device, a refractive property of the eye being measured with the aid of said third measuring device, measurement data of the measurements of the first, second and third measuring device being edited with the aid of said processing means, said processing means outputting the measurement data.

Apart from determining the refraction value objectively, measurement data for the topography or the curvature of the cornea as well as the axial length of the eye can be identified using the method. Owing to these measurement data, which are then available at the same time, a person carrying out the examination can more easily evaluate the measured refraction value. It is essential for the disclosure that the central axial length, which is located in the region of the visual axis, and the peripheral axial length, which is located outside of the region of the visual axis in the peripheral region of the retina outside of the fovea centralis, are measured as the axial length. If there is a case of axial myopia, different measurement data are commonly yielded for the central axial length and the peripheral axial length. On the basis of the measurement data that are output by the processing means, a person carrying out the examination is then in a position to evaluate whether there is a case of axial myopia or to what extent the retina is deformed within the fovea centralis with respect to the retina in the peripheral region. This means that through the measurement of the central axial length and of the peripheral axial length, a more comprehensive description of the examined eye can be obtained. With the aid of the obtained measurement data, improved optical corrections or visual aids can subsequently be calculated or selected.

During the measurement of the central axial length, the visual axis of the eye may be aligned with an optical measurement axis of the first measuring device, the visual axis of the eye being able to be inclined by an angle $\alpha > 0°$ in relation to the optical measurement axis of the first measuring device during the measurement of the peripheral axial length. The visual axis frequently runs in the central region of the retina starting from the fovea. A peripheral region of the retina starts in an outer edge zone of the macula or perifovea. The peripheral axial length is therefore measured starting from the peripheral region of the retina. In principle, the peripheral axial length may already be measured outside of the fovea centralis with an angle $\alpha$ of $\geq 1°40'$, outside of the fovea with an angle $\alpha \geq 5°$, outside of the parafovea with an angle $\alpha \geq 8°20'$ or outside of the perifovea with an angle $\alpha \geq 18°20'$.

The curvature of the cornea of the eye and the refractive property of the eye may be measured while the visual axis of the eye is aligned with the optical measurement axis of the first measuring device and/or while the visual axis of the eye is inclined by the angle $\alpha \geq 0°$ in relation to the optical measurement axis of the first measuring device. If the eye is inclined, for example, by the angle $\alpha$ in relation to the vision testing system for measuring the central axial length and for measuring the peripheral axial length, the curvature of the cornea and the refractive property of the eye may not only be measured during the measurement of the central axial length, but also during the measurement of the peripheral axial length. A measurement value for the refractive property of the eye then in particular is also yielded for the peripheral region of the retina at which the peripheral axial length is measured. In this way, testing the optical system of the eye becomes even more precise.

The visual axis of the eye may be inclined by an angle $\alpha$ of 20°, ±10° in relation to the optical measurement axis of the first measuring device during the measurement of the peripheral axial length. Through this comparatively strong incline of the visual axis in relation to the optical measurement axis, the peripheral region of the retina or of the focal cup of the eye that is curved correspondingly may advantageously be examined. The measurement data that are obtained in this region make it possible to determine or assess a myopia or axial myopia through a person carrying out the examination.

The peripheral axial length may be measured for different inclines of the visual axis of the eye in relation to the optical measurement axis of the first measuring device, the angle $\alpha$ being able to be changed in 5° increments. In this way, it is then, for example, possible to measure the peripheral axial length of the eye at many points of the retina. These points of measurement may also be distributed on concentric circles in relation to the visual axis so that a large number of measurement data of the respective peripheral axial lengths is obtained. If the refractive property of the eye is complementarily measured during each individual measurement of the respective peripheral axial length, a full coverage of the optical system of the eye becomes possible via the measurement data.

A peripheral fixation mark that can be focused on by the eye may be displayed by means of a fixation means of the vision testing system, the eye being able to focus on the fixation mark and the eye being to be fixated in relation to the vision testing system in this way. The peripheral fixation mark may be disposed in such a way that an optical axis of the eye or the visual axis of the eye is not aligned with the measurement axis of the first measuring device and in this way deviates from the same. The fixation mark may, for example, be a light emitting diode via which a visual stimulus is presented to the test person in question, said visual stimulus then bringing about an orientation of the eye in relation to the measurement axis of the first measuring device in the desired manner. The fact that the peripheral fixation mark is then located in close range of the eye and that the eye is also accommodated onto the peripheral fixation mark is not important for a measurement of the peripheral axial length. In contrast to this, determining a refractive property of an eye that is accommodated onto close range is only possible with errors so that a paralysis of the ciliary muscle (cycloplegia) would be required. It is in this way also possible to determine the refractive overall condition of the eye with measurement values for the peripheral axial length without cycloplegia.

A central fixation mark that can be focused on by the eye at infinity can be displayed by means of a fixation means of the vision testing system, the eye being able to focus on the fixation mark and the eye being able to be fixated in relation to the vision testing system. A correct positioning of the eye in relation to a measurement axis of the vision testing system is essential for a precise measurement of the vision testing system. Advantageously, an optical axis of the eye is aligned with the measurement axis of the vision testing system here. Here, the eye can be oriented by the fixation mark being presented to the test person, the test person being able to focus on said fixation mark at infinity. The fixation mark may be an image representation of an object, for example. A screen that is coupled to an optical path of the vision testing system may perform the image representation. It is essential that the image representation to the eye of the test person is at infinity so that the ciliary muscle of the eye is completely relaxed during the measurement with the aid of the vision testing system.

Advantageously, the eyes can then also be tested without administering cycloplegic agents. It is thus possible to test the eyes more easily and faster.

Different accommodation states of the eye of the test person can also be produced by means of a fixation means of the vision testing system. Here, a central axial length and/or a peripheral axial length of the eye as well as a refractive property of the eye can then be measured for each of the accommodation states. The measurement values that are obtained for the different accommodation states or different viewing positions of the eye can be used by the processing means to generate a comprehensive optical description of the eye. Using these measurement vales, improved optical corrections, for example glasses, contact lenses, intraocular lenses, phakic IOL, laser surgeries, can be calculated.

A measurement can be carried out on the eye using the first, second and third measuring device at the same time. The axial length, however, is measured in two steps.

If the axial length of the eye, the curvature of the cornea of the eye and the objective refractive property or a refraction value of the eye are simultaneously measured in diopters, for example, measurement errors as they may occur in successive measurements with the aid of different measuring instruments can be precluded. When the first, second and third measuring device perform measurements at the same time, all obtained measurement data refer to a state of the eye at this point in time, which makes it possible to compare the measurement data that were obtained under the same conditions. When using different apparatuses or when measurements are performed one after another, the eye is always oriented differently with respect to a measurement axis or is in different accommodation states as a consequence of eye movements.

A comparison of the central axial length to the peripheral axial length can be carried out and a result of said comparison can be output together with the measurement data by means of the processing means. Here, the processing means performs the comparison, outputting a result of said comparison and making it in this way possible for a person carrying out the examination to more easily evaluate the obtained measurement data. Here, the processing means comprises means for data processing and display functions, such as a computer and a screen.

Nonetheless, a comparison of the central measurement data to the peripheral axial length can also be carried out and a result of said comparison can be output together with the measurement data by means of the processing means. The central measurement data can then comprise, apart from the central axial length, measurement data on the objective refraction value and on the topography or curvature of the cornea. Owing to these measurement data, which are then available, a person carrying out the examination can more easily evaluate the measured refraction value.

A degree of refraction can be determined by means of the processing means through the comparison. With the aid of the degree of refraction, the identified measurement values of the axial lengths can be categorised on the basis of the deviation from the other measurement data. The processing means can identify a degree of an objective refraction on the basis of the physical quantities of the measurement values or measurement data. Here, the measurement values can be weighted differently or the measurement values can be put into relation to one another. The processing means can output the degree of the objective refraction, for example on a screen, so that it becomes possible to evaluate the refractive properties of the eye even more easily.

A refraction index and/or a refraction index gradient of the lens of the eye of the test person can be determined from the measurement data by means of the processing means. A refraction index of the lens of the eye changes with the age of a test person. The refraction index of the lens of the eye can also be different at different points of the lens. By measuring the peripheral axial length and at least the refractive property of the eye in the peripheral region, it becomes possible to also determine the refraction index of the lens of the eye, preferably the median or average refraction index, in this region. The refraction index gradient is then yielded with regard to the measurement data of the eye that are identified centrally.

The processing means may present a database with normal data, wherein it is possible to carry out a comparison of the measurement data to the normal data and to output a result of said comparison by means of said processing means. If the processing means carries out the comparison of the measurement data to the normal data, a deviation can easily be evaluated on the basis of the result of the comparison or of the respective difference of a measurement value from a normal value.

If, for example, a measurement value for the curvature of the cornea strongly deviates from a normal value, the person carrying out the examination can more easily interpret a refraction value that also deviates from the normal value. In the example that has been mentioned above, the curvature of the cornea may be the cause of the refraction value. Furthermore, a person carrying out the examination can determine a too large axial length as the reason for a refraction value. If there are no measurement values of the curvature of the cornea and of the axial length of the eye that deviate from a normal value, a refraction index of the lens may, for example, be different. All in all, it becomes possible, due to the fact that the measurement values are obtained at the same time, to obtain precise measurement values easily and quickly and to compare them to normal values.

Measurement data of eyes of a normal population, with a central axial length and/or a peripheral axial length of an eye, a curvature of the cornea of the eye and a refractive property of the eye, can be used as normal data.

The normal data can correspond to the fiftieth percentile of a comparison group of persons on whose eyes the measurement data were identified. The normal data may also include all measurement data of the comparison group, the processing means then being able to output a precise deviation of the measurement data that has been identified with the aid of the vision testing system from the fiftieth percentile of the comparison group, for example also an indication on to which percentile of the comparison group the measurement data can be assigned in each instance. A representative population average is understood to be the comparison group that is referred to as normal population here.

The processing means can in each instance compare the measured central axial length and/or the peripheral axial length, the curvature and the refractive property of the eye to the normal data of the central axial length and/or of the peripheral axial length, of the curvature and of the refractive property of an eye, said processing means being configured to select the normal data for the comparison according to a consistency of the central axial length and/or peripheral axial length, the curvature or the refractive property with the measurement data of the measurement.

The processing means can accordingly not only compare the respective records of measurement data and normal data for axial lengths, curvature and refractive property independently from one another, but it can also select, from the database or the normal data, an eye or the normal data and/or the measurement data associated with said eye that come closest to the measurement data that have been measured with the aid of the vision testing system or correspond to them. The processing means accordingly compares the eye measured with the aid of the vision testing system to the measurement data of the eyes that are stored in the database and outputs this comparison. Based on this comparison, a person carrying out the examination can evaluate even more easily to what extent the eye measured with the aid of the vision testing system deviates from a standard or already shows known symptoms.

The processing means can take an age of the test person into account when comparing the measurement data. The database having the normal data can likewise include normal data that can be assigned to a certain age in each instance. The processing means can then select the normal data for the comparison that correspond to the age of the test person from the database having the normal data. The age of the test person can, for example, be entered in the processing means via input means before or after a measurement. Owing to the known connection between myopia and age, an even more precise comparison of the measurement data becomes possible by taking into account the age of the test person. In addition, it is possible that the processing means for example takes a prevalence of myopia in the population into account when comparing the measurement data. Apart from age, job profiles and dispositions can then also be taken into account.

Measurement data of the test person that were determined at a point of time before the measurement can be used as normal data, said measurement data having a peripheral and/or central axial length of the eye, a curvature of the cornea of the eye and a refractive property of the eye. With the aid of the vision testing system, it is in this way possible to take measurements of the same test person at different points of time and to obtain and store measurement data in each instance. These measurement data can then be used as normal data for the comparison. In this way, a potential change in the optical property of the eye in question can be determined over a period of months or years, for example. A cause of a deteriorating refraction value, for example, can in this way be identified even more easily. Optionally, it is also possible, however, to always compare the measurement data measured at each measuring time to normal data of a comparison group.

The processing means can correct the measurement data of the third measuring device with the aid of the measurement data of the first measuring device and/or of the second measuring device. Determining an objective refraction value is often difficult and prone to errors since the refractions may be influenced by many factors and environmental conditions, as pointed out above. The curvature of the cornea and the axial length, however, are measurement values that are not subject to the influence of medication or brain activity, for example. The measurement data of the third measuring device can therefore advantageously be corrected with the aid of the measurement data of the first and/or second measuring device.

In this way, the processing means is configured to carry out a plausibility check for a measured objective refraction value of the eye with the central and/or peripheral axial length and/or with the curvature of the cornea of the eye and to correct said refraction value according to the central and/or peripheral axial length and/or the curvature of the cornea when the refraction value differs. Here, the plausibility check can be performed on the basis of range indications that state a tolerance range for the respective measurement values. The range indications may also be stored in the database. The range indications may be based on experience or may be determined on the basis of a standard deviation with the aid of statistical averages.

The vision testing system in accordance with the disclosure for testing the eyes of a test person comprises a first measuring device, a second topographic measuring device, a third refractive measuring device and a processing means, a central axial length and a peripheral axial length of an eye of the test person being measured with the aid of said first measuring device, a curvature of the cornea of the eye being measured with the aid of said second measuring device, a refractive property of the eye being measured with the aid of said third measuring device, said processing means being configured to edit measurement data of the measurements of the first, second and third measuring device, said vision testing system presenting a fixation means, the eye being able to be fixated in relation to the vision testing system by means of the fixation means either for measuring the central axial length or the peripheral axial length. With regard to the advantages of the vision testing system in accordance with the disclosure, reference is made to the description of the advantages of the method in accordance with the disclosure.

It is particularly advantageous if the first, second and third measuring device are integrated in one piece of equipment.

The fixation means may comprise a central fixation mark that is configured to be displayed at infinity to the eye and is configured to be focused on by the eye, said central fixation mark being disposed in such a manner that a visual axis of the eye can be aligned with an optical measurement axis of the first measuring device when the central fixation mark is being focused on by the eye. In principle, the first measuring device, the second measuring device and/or the third measuring device can include the fixation means.

The fixation means may, for example, comprise a screen or a suitable projector, with the aid of which the central fixation mark can be visibly represented to the eye at infinity. The central fixation mark may be an image representation of an object so that a focusing of the eye on a dot is avoided. The central fixation mark may be coupled to an optical path of the vision testing system via, for example, a splitter cube so that the central fixation mark is visible for the test person.

Furthermore, the fixation means can comprise a peripheral fixation mark that is configured to be displayed to the eye and is configured to be focused on by the eye, said peripheral fixation mark being disposable in such a manner that a visual axis of the eye can be inclined by an angle $\alpha>0°$ in relation to an optical measurement axis of the first measuring device when the peripheral fixation mark is being focused on by the eye.

The peripheral fixation mark may be realised by at least one light emitting diode that can be disposed, in relation to the optical measurement axis, eccentrically at a housing side of the vision testing system facing the eye. A test person can then be positioned in front of the housing side of the vision testing system facing her or him, an eye movement of an eye of the test person being able to be effected easily by the light emitting diode being disposed eccentrically on the housing side or the housing of the vision testing system at some distance from the optical measurement axis and by it producing a light stimulus. With the aid of a light emitting diode, a fixation mark can be realised at particularly low costs. Furthermore, it may also be envisaged to dispose a plurality of light emitting diodes coaxially around the optical measurement axis in order to initiate a movement of the eye in a desired direction. In addition, multiple light emitting diodes can also be attached to the housing side at different intervals in relation to the optical measurement axis in order to effect a pivoting of the eye by different angles $\alpha$ in relation to the optical measurement axis. Nonetheless, the one light emitting diode may also be realised so as to be adjustable in respect of its relative position with respect to the optical measurement axis.

The fixation means may comprise an optical deflexion element which is configured to be pivoted into an optical path of the central fixation mark and using which the optical path of the central fixation mark can be deflected in such a manner that the central fixation mark can be displayed as a peripheral fixation mark, in relation to the optical measurement axis, eccentrically on a housing side of the vision testing system facing the eye. If, for example, the central fixation mark is realised by a screen or by another suitable projector, an optical path that comes from the screen can be deflected with the aid of the optical deflexion element, which may be a mirror or a prism, for example, in such a way that the optical path is no longer aligned with the optical measurement axis or runs parallel to the same. The optical deflexion element may, for example, be a movable tilting mirror that can be pivoted into and out of the optical path of the central fixation mark as required. Then, it is, by the way, also possible to present a peripheral fixation mark to the eye that can be focused at infinity.

The first measuring device, the second measuring device and the third measuring device may present a common measurement axis that can be harmonised with an optical axis of the eye. Due to the fact that the measuring devices present a common measurement axis, it becomes possible to obtain measurement data that are particularly precise and can be compared particularly well. It is in particular advantageous for precisely determining an axial length of the eye if the shared measurement axis is aligned with the optical axis of the eye.

The second measuring device and/or the third measuring device may present a distance measurement means for measuring a distance between the eye and the second measuring device and/or third measuring device. The distance measurement means can measure the distance between the refractive measuring device and/or the topographic measuring device and the eye to be examined. This distance is essential for a correction of the measurement data and it becomes possible by obtaining distance data to correctly position the test person in front of the vision testing system accordingly or to suitably correct the measurement data that have been measured with the aid of the refractive measuring device. In this way, the distance between the refractive measuring device and the cornea of the eye, in particular the front face of the cornea, may advantageously be measurable with the aid of the distance measurement means. In addition, a distance from the retina or rear face of the eye can also be determined with the aid of the distance measurement means while taking into account the axial length. Optionally, a distance from a rear face of the cornea, a front face of the lens and/or a rear face of the lens can also be determined. The type of construction of the distance measurement means is in principle arbitrary, said distance measurement means being realisable by the topographic measuring device, by a keratometer or by a Scheimpflug system.

The first measuring device may be an ultrasonic measuring device or an interferometric measuring device. In principle, the first measuring device may be any type of measuring device with the aid of which a central axial length and a peripheral axial length of an eye can be measured.

Furthermore, the first measuring device may be an interferometer for optical coherence interferometry (OCT).

As an alternative, the first measuring device may be a partial coherence interferometer (PCI), said interferometer being configured to have a coherent light source, two measuring arms and a detector means for simultaneously capturing the front face of the cornea and of the retina or an optical boundary surface of the eye. Due to the fact that the interferometer disposes of two measuring arms, it is possible to simultaneously detect the front face of the eye and the retina and to determine a relative distance between the front face and the retina and consequently the central and/or peripheral axial length of the eye. Here, it is not essential how far the eye is from the vision testing system since the distance measurement or the measurement of the axial lengths of the eye can be carried out with the aid of the interferometer irrespectively of the distance from the vision testing system. Possible measurement errors of the interferometer owing to a distance position of the eye in relation to the vision testing system can in this way be entirely precluded. The axial lengths can consequently be measured particularly precisely. Apart from the axial lengths, other optical boundary surfaces of the eye, such as the rear face of the cornea, the front face of the lens, the rear face of the lens, and distances between the optical boundary surfaces can moreover be measured with the aid of the interferometer and be processed by the processing means. These measurement data can likewise be utilised by the processing means for a comparison to corresponding normal data.

The second measuring device may be a keratometer and/or a Scheimpflug system. With the aid of such measuring devices, it is possible to determine a topography or the curvature of the cornea of the eye.

The keratometer may present an examination means having a camera and measuring marks that can be captured with the aid of the camera and that can be realised by a fluorescent strip that is circular and not collimated and by two collimated luminous spots. A type of construction of the measuring marks of the keratometer is basically arbitrary, light emitting diodes being envisagable as an illuminant. The fluorescent strip may be generated by a circular light conductor element. It may also be envisaged to generate a plurality of concentric annular fluorescent strips. Advantageously infrared light may be used as the light for the measuring marks. The examination means may be a camera that is coupled to an optical path of the vision testing system or of the keratometer via a splitter cube. With the aid of the camera, a parasitic image of the measuring marks on the cornea of the eye can be captured. By means of image processing, a curvature of the cornea can easily be derived from the parasitic image of the measuring marks and be displayed by the processing means. Furthermore, it is possible to use the camera as a setup camera or as an overview camera for the vision testing system for the precise disposition and orientation of the eye of the test person.

The Scheimpflug system may present a projection means that may be designed for illuminating the eye with a light gap and an examination means having a camera that may be designed for capturing a sectional view of the light gap in the eye, said projection means and the camera being configured to be disposed in relation to each other according to the Scheimpflug principle. With the aid of the projection means, the light gap can then be projected onto the eye so that a gap illumination of the eye along the optical axis of the eye or of the visual axis can be performed. With the aid of the camera that is disposed according to the Scheimpflug principle, the sectional view of the light gap in the eye that is generated in this way can be captured so that an illuminated cross-sectional area of the eye or a front portion of the eye can be captured optically. A longitudinal sectional view of the eye that results in this way can then advantageously reproduce the optical boundary surfaces of the cornea and of the lens. The processing means can easily calculate the relative distances of the optical boundary surfaces from a set of image data that has been obtained in this way. Furthermore, the curvature of the cornea can also easily be identified. The Scheimpflug system may realise the second measuring device alone or together with the keratometer.

Advantageously, the third measuring device may be an autorefractometer.

The autorefractometer may present a projection means that may be designed for projecting a lighting pattern onto the retina of the eye and an examination means that has a diffraction unit and a camera and that may be designed for capturing the lighting pattern in the eye. Here, the lighting pattern may be projected in such a way that the lighting pattern is focused on the retina. With the aid of the optical examination means, the lighting pattern that is reflected on the retina can be examined through the lens of the eye so that an image pattern is displayed on a photoelectric sensor of the camera. This image pattern is captured by the camera and is analysed by means of image editing. Corresponding to the refractive properties of the eye, the lighting pattern that is projected onto the retina is characteristically distorted so that the refractive properties of the eye can be derived within the framework of analysing the lighting pattern from a degree of distortion. The diffraction unit may, for example, be an aperture plate having a number of holes that are disposed in a circle, the optical paths of the holes in each instance being deflectable onto the sensor of the camera via a deflection prism or a corresponding lens. Alternatively, the diffraction unit may also be a diffractive optical element (DOE).

Other advantageous embodiments of a vision testing system result from the description of the features contained in the dependent claims that relate to method claim 1.

In the following, the disclosure is explained in more detail with reference to the enclosed drawing.

Figure 1:
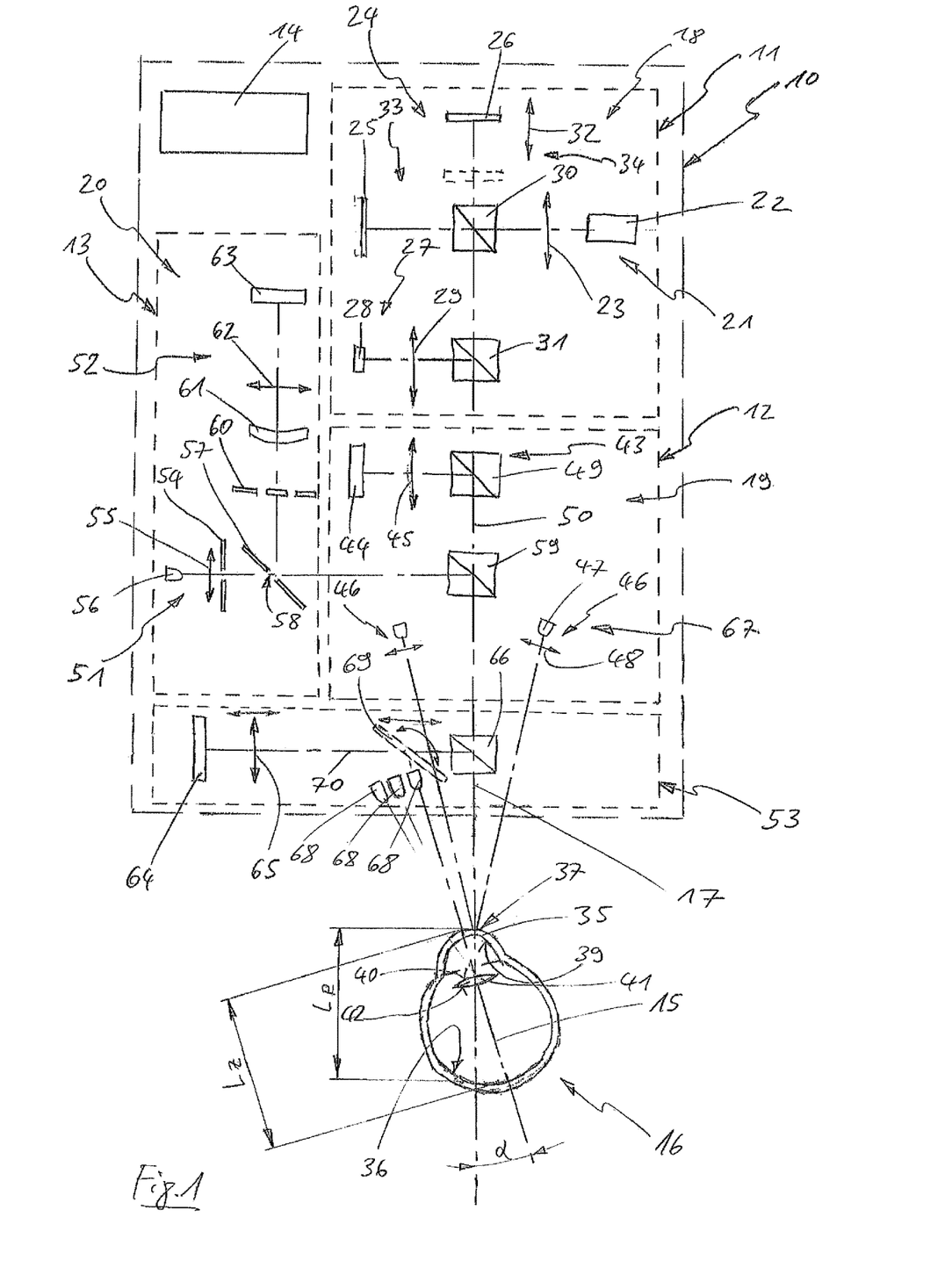
FIG. 1 shows a schematic illustration of a vision testing system.

FIG. 1 shows a schematic illustration of a construction of a vision testing system 10 comprising a first interferometric measuring device 11, a second topographic measuring device 12, a third refractive measuring device 13 and a processing means 14. The vision testing system 10 is disposed in relation to a visual axis 15 or optical axis of an eye 16 to be examined in such a way that the visual axis 15 does not correspond to a measurement axis 17 of the vision testing system 10 or deviates from the same. In this way, the visual axis 15 of the eye 16 is inclined by an angle α in relation to the optical measurement axis 17. The first interferometric measuring device 11 is realised by a partial coherence interferometer 18, the second topographic measuring device 12 is realised by a keratometer 19 and the third refractive measuring device 13 is realised by an autorefractometer 20.

The interferometer 18 is essentially made up of a laser means 21 having a laser light source 22 and a lens arrangement 23, a mirror means 24 having a first mirror 25 and a second mirror 26, a detector means 27 having a detector 28 and a lens arrangement 29 as well as a first splitter cube 30 and a second splitter cube 31. In particular the second mirror 26 is disposed so as to be longitudinally displaceable along the double arrow 32 so that a length of a second reference arm 34 or of a corresponding reference path can be changed. A first reference arm 33 is, however, not realised in such a way that its length can be changed. Through a displacement of the second mirror 26, different regions of the eye 16 that are located on the visual axis 15 can be scanned. In particular, it is possible to measure a central axial length ($L_Z$) and a peripheral axial length ($L_P$) of the eye 16 from the cornea 35 up to the retina 36 or from a front face 37 of the cornea 35 up to a rear face 38 of the retina 36. A more in-depth explanation of a known function of the partial coherence interferometer 18 is omitted here. Furthermore, measurement data may also be obtained that describe relative positions of optical boundary surfaces on the visual axis 15, such as the front face 37 of the cornea 35, the rear face 39 of the cornea 35, a front face 40 of a lens 41, a rear face 42 o the lens 41 and the rear face 38 of the retina 36.

The keratometer 19 comprises an examination means 43 having a camera 44 and a lens arrangement 45 as well as measuring marks 46 that can be captured with the aid of the camera 44 and that are realised by an infrared light source 47 and by a lens arrangement 48 in each instance. The infrared light source may be a light emitting diode, for example. The measuring marks 46 may realise two collimated luminous spots on the cornea 35 that can both be captured with the aid of the camera 44. The measuring marks 46 are supplemented by a fluorescent strip that is circular, not collimated and not illustrated. The examination means 43 is coupled to an optical path 50 of the vision testing system 10 via a splitter cube 49.

The autorefractometer 20 serves for determining the refractive properties of the eye 16 and essentially comprises a projection means 51 and an examination means 52 as well as a fixation means 53, which may, however, also be realised independently from the autorefractometer 20. With the aid of the optical projection means 51, a lighting pattern can be projected onto the retina 36 of the eye 16 and be focused there. Here, the projection means 51 comprises an aperture plate 54, a lens arrangement 55 and an infrared light source 56. The lighting pattern is coupled to the optical path 50 of the vision testing system via a mirror 57 having an aperture plate 58 via a first splitter cube 59 of the autorefractometer 20. The optical examination means 52 comprises a 6-fold aperture plate 60, a deflection prism 61, a lens arrangement 62 and a camera 63. The image data that are captured with the aid of the camera 63 are processed and analysed in the processing means 14 in order to determine the refractive properties of the eye 16. The examination means 52 is coupled to the optical path 50 via the mirror 57 and the first splitter cube 59.

The fixation means 53 of the autorefractometer 20 is realised by a screen 64 for the image representation of a central fixation mark and by a lens arrangement 65 for displaying the central fixation mark at infinity.

The lens arrangement 65 can be moved in the direction of an optical path 70 of the screen 64 in order to be able to set different accommodation states or different vision distances of the eye 16. A second splitter cube 66 makes it possible to couple the central fixation mark to the optical path 50. The first splitter cube 59 and the second splitter cube 66 are then parts of the autorefractometer 20.

The fixation means 53 of the autorefractometer 20 furthermore comprises a peripheral fixation mark that is configured to be displayed to the eye 16 and is configured to be focused on by the eye 16 and that can be realised by one of the light emitting diodes 68 here. The light emitting diodes 68 are disposed, in relation to the optical measurement axis 17, eccentrically at a housing side of the vision testing system 10 that faces the eye 16 and is not illustrated here. For illustrating a peripheral fixation mark, one of the light emitting diodes 68 is lit so that, owing to the light stimulus that has been generated, a rotation of the eye 16 around the angle α, where the visual axis 15 is in relation to the measurement axis 17, is effected along with an accommodation onto the peripheral fixation mark. In this way, it is then possible to measure the peripheral axial length $L_P$ of the eye with the aid of the interferometer 18. Depending on which light emitting diode 68 is used for presenting the peripheral fixation mark, the peripheral axial length $L_P$ can be measured at different inclines of the visual axis 15 by the angle α in relation to the measurement axis 17. The fact that there is an accommodation of the eye at close range when the peripheral fixation mark is being displayed is not relevant for the measurement of the peripheral axial length $A_P$. Since the central axial length $A_Z$ is measured before or after the measurement of the peripheral axial length $A_P$, the processing means 14 can carry out a comparison of the central axial length $A_Z$ to the peripheral axial length $A_P$ and output a result of said comparison together with the rest of the measurement data. Depending on a ratio of the axial lengths $A_P$ to $A_Z$, a person carrying out the examination can then evaluate a refractive property of the eye 16.

As an alternative, the fixation means 53 may present a tilting mirror 69 that can be pivoted into the optical path 70 of the screen 64 and of the lens arrangement 65 or of the central fixation mark. The optical path 70 can then be deflected by means of the tilting mirror 69 even before the second splitter cube 66 and be directed at the eye 16 at the angle α in relation to the measurement axis 17. The central fixation mark is thereafter presented to the eye 16 as a peripheral fixation mark. It is advantageous here that the eye 16 is also able to accommodate the peripheral fixation mark at infinity. Apart from measuring the peripheral axial length $L_P$, the measurement of a refractive property of the eye 16 is then also possible with the aid of the autorefractometer 20 without administering cycloplegic agents. The fixation means 53 may also be realised so as to be rotatable about the measurement axis 17 so that the peripheral fixation mark can be presented at almost any point in the visual field of the eye 16.

Furthermore, a distance measurement means 67 is envisaged that is realised by the keratometer 19 here. The distance measurement means 67 comprises the measuring marks 46 and the examination means 43.

With the vision testing system 10 that is illustrated here, a measurement is performed at the same time with the first measuring device 11, the second measuring device 12 and the third measuring device 13, the processing means 14 processing measurement data of the measurement of the first measuring device 11, the second measuring device 12 and the third measuring device 13, said processing means 14 presenting a database that is not illustrated here, having normal data, a comparison of the measurement data to the normal data being carried out and a result of said comparison being output by means of said processing means 14.

Figure 2:
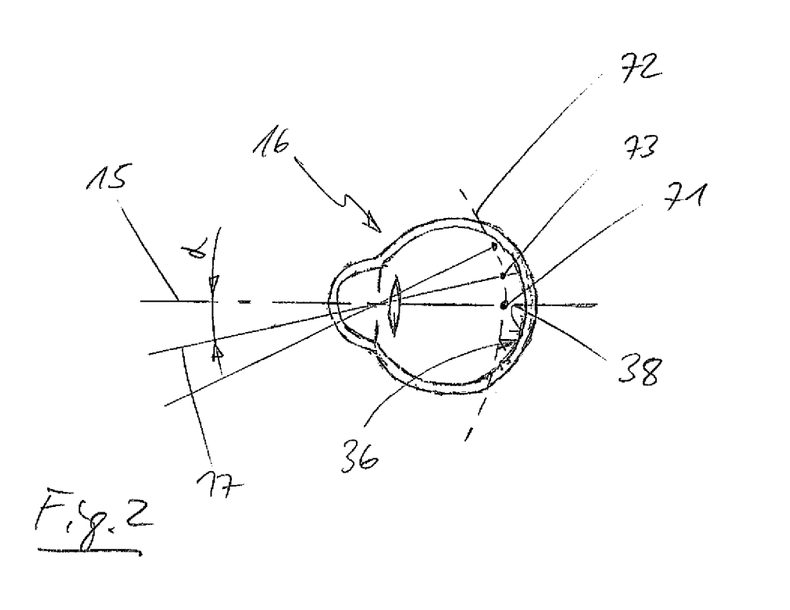
FIG. 2 shows a sectional view of an eye.

FIG. 2 shows the eye 16 together with the visual axis 15 and a focus 71 on the visual axis 15 of a well-focused image in a cup-shaped focal plane 72 or a focal cup of the eye 16. The focus 71 is in front of the rear face 38 of the retina 36 here so that the eye 16 is myopic. When the measurement axis 17 is pivoted by the angle α in relation to the visual axis 15, a focus 73 is yielded that is closer to the rear face 38 in comparison to focus 71. From this, a shape of the cup-shaped focal plane 72 is yielded. In order to achieve the best possible correction of the myopia of the eye 16, it is now required to not only shift the focus 71 onto the rear face 38 by means of a visual aid or of an invasive surgical intervention, but to also adapt the cup-shaped focal plane 72 correspondingly to the shape of the retina 36. This adaptation only becomes possible if there is knowledge of the optical properties of the eye 16 in the peripheral region of the retina 36. In order to prevent a myopia from advancing further, for example in adolescents, the cup-shaped focal plane 72 can be arched more tightly through a corresponding selection of a visual aid in excess of a curvature of the retina 36. Apart from the refractive properties of the eye 16, knowledge of the central axial length $L_Z$ and of the peripheral axial length LP of the eye 16 is particularly important here.

The invention claimed is:

1. A method for testing the eyes of a test person with the aid of a vision testing system, comprising a fixation means, a first measuring device, a second topographic measuring device, a third refractive measuring device and a processing means, the method comprising the following steps:
   fixing the eye in relation to the vision testing system either for measuring a central axial length ($L_Z$) or a peripheral axial length ($L_P$) with the aid of the fixation means, the fixation means comprising a peripheral fixation mark configured to be displayed for and focused on by the eye, the fixation mark being disposed such that a visual axis of the eye is not aligned with a measurement axis of the first measuring device;
   measuring the central axial length ($L_Z$) and the peripheral axial length ($L_P$) of an eye of the test person with the aid of said first measuring device;
   measuring a curvature of the cornea of the eye with the aid of said second measuring device;
   measuring a refractive property of the eye with the aid of said third measuring device; and
   processing measurement data of the measurements of the first, second and third measuring device with the aid of said processing means, said processing means outputting the measurement data.

2. The method according to claim 1, wherein during the measurement of the central axial length ($L_Z$), the visual axis of the eye is aligned with an optical measurement axis of the first measuring device, the visual axis of the eye being inclined by an angle α>0° in relation to the optical measurement axis of the first measuring device during the measurement of the peripheral axial length ($L_P$).

3. The method according to claim 2, wherein the curvature of the cornea of the eye and the refractive property of the eye are measured while the visual axis of the eye is aligned with the optical measurement axis of the first measuring device and/or while the visual axis of the eye is inclined by the angle α>0° in relation to the optical measurement axis of the first measuring device.

4. The method according to claim 2, wherein the visual axis of the eye is inclined by an angle α of 20°, ±10° in relation to the optical measurement axis of the first measuring device during the measurement of the peripheral axial length ($L_P$).

5. The method according to claim 2, wherein the peripheral axial length ($L_P$) is measured for different inclines of the visual axis of the eye in relation to the optical measurement axis of the first measuring device, the angle α being changed in 5° increments.

6. The method according to claim 1, wherein a peripheral fixation mark that can be focused on by the eye is displayed by means of a fixation means of the vision testing system, the eye focusing on the fixation mark and the eye being fixated in relation to the vision testing system.

7. The method according to claim 1, wherein a central fixation mark that can be focused on by the eye at infinity is displayed by means of a fixation means of the vision testing system, the eye focusing on the fixation mark and the eye being fixated in relation to the vision testing system.

8. The method according to claim 1 wherein different accommodation states of the eye of the test person are produced by means of a fixation means of the vision testing.

9. The method according to claim 1, wherein a measurement of the eye is carried out using the first, second and third measuring device at the same time.

10. The method according to claim 1, wherein by means of the processing means, a comparison of the central axial length ($L_Z$) to the peripheral axial length ($L_P$) is carried out and a result of said comparison is output together with the measurement data.

11. The method according to claim 1, wherein by means of the processing means, a comparison of the central measurement data to the peripheral axial length ($L_P$) is carried out and a result of said comparison is output together with the measurement data.

12. The method according to claim 1, wherein a degree of refraction is determined by means of the processing means through the comparison.

13. The method according claim 1, wherein a refraction index and/or a refraction index gradient of the lens of the eye of the test person is/are determined from the measurement data by means of the processing means.

14. The method according to claim 1, wherein the processing means presents a database with normal data, a comparison of the measurement data to the normal data being carried out and a result of said comparison being output by means of said processing means.

15. The method according to claim 14, wherein measurement data of eyes of a normal population, with a central axial length ($L_Z$) and/or a peripheral axial length ($L_P$) of an eye, a curvature of the cornea of the eye and a refractive property of the eye, are used as normal data.

16. The method according to claim 14, wherein the processing means in each instance compares the measured central axial length ($L_Z$) and/or the peripheral axial length ($L_P$), the curvature and the refractive property of the eye to the normal data of the central axial length ($L_Z$) and/or of the peripheral axial length ($L_P$), of the curvature and of the refractive property of an eye, said processing means selecting the normal data for the comparison according to a consistency of the central axial length ($L_Z$) and/or peripheral axial length ($L_P$), the curvature or the refractive property with the measurement data of the measurement.

17. A vision testing system for testing the eyes of a test person, comprising a first measuring device, a second topographic measuring device, a third refractive measuring device and a processing means, a central axial length ($L_Z$) and a peripheral axial length ($L_P$) of an eye of the test person being measured with the aid of said first measuring device, a curvature of the cornea of the eye being measured with the aid of said second measuring device, a refractive property of the eye being measured with the aid of said third measuring device, said processing means being configured to process measurement data of the measurements of the first, second and third measuring device, said vision testing system presenting a fixation means, the fixation means configured to fix the eye in relation to the vision testing system for measuring the central axial length ($L_Z$) or the peripheral axial length ($L_P$), the fixation means comprising a peripheral fixation mark, the peripheral fixation mark configured to be displayed for and to be focused on by the eye in such a manner that a visual axis of the eye is not aligned with the measurement axis of the first measurement device.

18. The vision testing system according to claim 17, wherein the first, second and third measuring device are integrated in one piece of equipment.

19. The vision testing system according to claim 17 wherein the fixation means comprises a central fixation mark that is configured to be displayed at infinity for the eye and is configured to be focused on by the eye, said central fixation mark being disposed in such a manner that a visual axis of the eye is aligned with an optical measurement axis of the first measuring device when the central fixation mark is being focused on by the eye.

20. The vision testing system according to claim 17, wherein the peripheral fixation mark is disposed in such a manner that a visual axis of the eye is inclined by an angle $\alpha > 0°$ in relation to an optical measurement axis of the first measuring device when the peripheral fixation mark is being focused on by the eye.

21. The vision testing system according to claim 17, wherein the peripheral fixation mark is realised by at least one light emitting diode that is disposed, in relation to the optical measurement axis, eccentrically on a housing side of the vision testing system facing the eye.

22. The vision testing system according to claim 20, wherein the fixation means comprises an optical deflexion element which is configured to be pivoted into an optical path of the central fixation mark and using which the optical path of the central fixation mark can be deflected in such a manner that the central fixation mark can be displayed as a peripheral fixation mark, in relation to the optical measurement axis, eccentrically on a housing side of the vision testing system facing the eye.

23. The vision testing system according to claim 17, the first measuring device, the second measuring device and the third measuring device-present a common measurement axis that can be harmonised with the optical axis of the eye.

24. The vision testing system according to claim 17, wherein the first measuring device is an ultrasonic measuring device or an interferometric measuring device.

25. The vision testing system according to claim 24, wherein the first measuring device is an interferometer for optical coherence interferometry (OCT).

26. The vision testing system according to claim 24, wherein the first measuring device is a partial coherence interferometer, said interferometer being designed to have a coherent light source, two measuring arms and a detector means for simultaneously capturing the front face and the retina of the eye.

27. The vision testing system according to claim 17, wherein the second measuring device is a keratometer and/or a Scheimpflug system.

28. The vision testing system according to claim 17, wherein the third measuring device is an autorefractometer.

* * * * *

UNITED STATES PATENT AND TRADEMARK OFFICE
CERTIFICATE OF CORRECTION

PATENT NO. : 11,723,533 B2
APPLICATION NO. : 16/809818
DATED : August 15, 2023
INVENTOR(S) : Andreas Steinmueller It is certified that error appears in the above-identified patent and that said Letters Patent is hereby corrected as shown below:

In the Specification

Column 13, Line 53, "LP" should be --$L_P$--.

Signed and Sealed this
Seventeenth Day of October, 2023

Katherine Kelly Vidal
*Director of the United States Patent and Trademark Office*